United States Patent [19]

Bradshaw

[11] 4,063,452
[45] Dec. 20, 1977

[54] METHOD AND DEVICE FOR MONITORING VAPOR CONCENTRATION AT A PHASE INTERFACE

[75] Inventor: Thomas Ian Bradshaw, Shoreview, Minn.

[73] Assignee: Minnesota Mining and Manufacturing Company, Saint Paul, Minn.

[21] Appl. No.: 658,114

[22] Filed: Feb. 13, 1976

Related U.S. Application Data

[63] Continuation-in-part of Ser. No. 591,329, June 30, 1975, abandoned.

[51] Int. Cl.² .............................................. G01N 19/10
[52] U.S. Cl. ................................. 73/73; 116/114 AM
[58] Field of Search ...................... 73/29, 73, 76, 335; 116/114 AM

[56] References Cited

U.S. PATENT DOCUMENTS

| | | | |
|---|---|---|---|
| 2,249,867 | 7/1941 | Snelling | 73/335 |
| 2,504,299 | 4/1950 | Cartwright | 116/114 AM X |
| 3,018,611 | 1/1962 | Biritz | 116/114 AM X |
| 3,019,638 | 2/1962 | Klein | 73/73 |
| 3,142,287 | 7/1964 | Jones | 73/73 X |
| 3,198,163 | 8/1965 | Williams | 116/114 AM |
| 3,680,364 | 8/1972 | Carrier | 73/73 |
| 3,744,295 | 7/1973 | Allinikov | 252/408 X |
| 3,788,128 | 1/1974 | Strohecker | 73/73 |
| 3,824,844 | 7/1974 | Strickland | 73/73 |
| 3,951,098 | 4/1976 | Meyers | 73/73 X |

Primary Examiner—Richard C. Queisser
Assistant Examiner—John S. Appleman
Attorney, Agent, or Firm—Cruzan Alexander; Donald M. Sell; Warren R. Bovee

[57] ABSTRACT

Method of monitoring and indicating the concentration of vapor components at a phase interface comprising sampling vapor at the vapor source phase interface, comparing the vapor concentration in the sample with a standard, and indicating the concentration of the vapor relative to the standard. A monitoring device is disclosed which comprises a sensing means and means for responsively coupling the sensing means to the vapor source phase to be monitored so that a representative vapor sample is presented to the sensing means. The method and device disclosed herein can be advantageously used to monitor volatile components, especially moisture, available to potted plants.

17 Claims, 4 Drawing Figures

METHOD AND DEVICE FOR MONITORING VAPOR CONCENTRATION AT A PHASE INTERFACE

This application is a continuation-in-part of copending application Ser. No. 591,329, filed June 30, 1975, abandoned.

The present invention relates to a method and device for monitoring and indicating the concentration of a selected vapor component at a phase interface. The measured concentration is related to a parametric concentration of the vapor and the concentration of vapor relative to the parametric concentration is indicated.

In a preferred embodiment, the present invention relates to a method and device for continuously monitoring and indicating concentrations of volatile components, e.g. moisture, in soil. The method comprises sampling selected vapors present at the surface of the soil, comparing the vapor concentration in the sample with a standard, and indicating the concentration of a corresponding volatile component in the soil.

Monitoring devices are disclosed which perform the described functions. The monitoring devices comprise sensing and comparing means enclosed within a moisture-impermeable, vapor-permeable envelope. The disclosed devices are adapted to be located at a phase interface from which a vapor is issuing and can effectively sample and indicate the concentration of various selected vapors at the interface. This concentration can then be compared to a standard representative of some parametric concentration of the vapor which can be related to the concentration of a corresponding unvaporized volatile component from which the vapor issues, a chemical reactant or agent causing formation of the vapor or the like. The concentration of the vapor relative to the standard is indicated by the device such as by a visible color change.

The method and monitoring devices disclosed herein can be used to particular advantage for monitoring the moisture available to potted plants and can visibly indicate the point at which the soils containing the plants should be watered. Alternatively, the method and devices can be used to monitor the concentration of other volatile components, such as ammonia, in soil and visibly indicate their concentration. The devices can also be used to indicate the presence of moisture in diapers, surgical dressings, or the like, as will be described in greater detail hereinafter.

Devices for monitoring the moisture content of the soil around potted plants are known. These devices generally employ a wick with a color indicator associated therewith which indicates the presence of moisture in the wick when the wick is submerged in the soil near the plant. A change in color indicates the need to water the soil. U.S. Pat. Nos. 3,019,638 and 3,702,755 exemplify devices of this type.

These wick-type devices do not operate satisfactorily under certain conditions. In some cases the construction of these devices causes the wick to dry prematurely by evaporation and the device does not reflect the actual status of the soil's moisture condition. Furthermore, wicks tend to concentrate water soluble materials within their structure and thereby become less transmissive, particularly the portion above the soil's surface where the wicks can dry out and actually become hydrophobic and inoperative due to the build-up of these water soluble residues. These phenomena can produce inaccurate readings which may cause the plant to be watered more often than necessary, resulting in plant damage. Cellulosic wicks tend to degrade within a short time and may require replacement of these indicating devices rather frequently.

U.S. Pat. No. 3,788,128 discloses a device for determining the moisture content of soil at a distance below the surface of the soil. The device is adapted to be submerged in the soil and contains one or more indicating members adjacent a cavity within the device and separated therefrom by a membrane which is permeable to moisture but not to liquid water. The cavity communicates with the soil through water-vapor permeable passages. The indicating members change color in response to a specific humidity range in the cavity. By determining the temperature and the amount of humidity in the subsoil, the device aids in determining the optimum concentration of seed to be sown.

U.S. Pat. No. 3,680,364 discloses a humidity monitoring device for curing concrete. The device comprises a chamber having a base member and a viewing cover and containing therewithin a humidity indicating element. The base portion of the chamber is permeable to moisture, while the remainder of the chamber is impermeable to moisture. The device is placed on the surface of, or is pressed into the surface of, curing concrete and visibly indicates, by a color change, when the concrete requires watering for proper hydration.

U.S. Pat. No. 3,004,895 discloses a device for absorbing large quantities of ammonia. The absorbing agent is enclosed within a liquid impermeable, ammonia permeable envelope. An indicating material is included in the envelope which changes color when the absorbing agent is depleted.

According to the present invention a relatively simple, but effective, method and device are provided for monitoring and indicating the concentration of vapor at a phase interface such as a solid/gas, liquid/gas or even a gas/gas interface, the device itself being preferably located in the gas phase which is not the source of the vapor and which is usually air. The method comprises (1) obtaining substantially directly from the surface of the source phase from which the vapor issues, a representative sample containing a selected vapor component which has been released from the source phase to be monitored; (2) comparing the concentration of the vapor in the sample with a standard which is representative of a selected parametric concentration of the vapor; and (3) indicating the concentration of the vapor component in the sample relative to the standard.

The parametric concentration which is selected can be a vapor concentration which is deleterious or advantageous in itself or can be a concentration which can be related to a concentration of the vapor in the source phase from which the vapor issues, the concentration of a corresponding volatile component in the source phase, the concentration of a chemical reactant or agent which acts to produce the vapor within the source phase, or the like. Thus, the method and device can be used to monitor the moisture in soil as well as detect and indicate the presence of moisture in diapers, surgical dressings and other absorbent materials. The invention also has utility in the detection and indication of vapors other than moisture vapor, e.g. ammonia, contained in or issuing from soil, water, decomposing proteinaceous material or other sources.

The monitoring device according to the present invention comprises a sensing means for comparing the concentration of a selected vapor component in a sample with a standard which is representative of a selected parametric concentration of the vapor in the sample. The sensing means can also include, or have associated therewith, means for indicating the concentration of the selected vapor in the sample relative to the standard. Typical sensing and indicating means are materials which change color or other optical, chemical or electrical properties in response to exposure to a given concentration of a vapor component, e.g. cobalt chloride for sensing moisture vapor; alizarin or pH papers for sensing ammonia.

The monitoring device also includes, in combination with the sensing and indicating means, a liquid-impermeable, vapor-permeable envelope enclosing the sensing means. The envelope comprises a base and a cover wherein the base is adapted to rest on or otherwise communicate with the phase from which the vapor issues. The base transmits vapor at a rate greater than the cover. Preferably the base has a vapor transmission rate at least about 50% greater than the cover and most preferably at least about 100% greater than the cover.

As noted, the base of the device can rest directly on the vapor source phase or otherwise be fastened in contact with the vapor source phase. Alternatively, the base can be spaced from the source phase if other means, such as a tube or other connecting means, is used to maintain the base in communication with the vapor source phase so that the device can effectively sample the vapor issuing therefrom.

The differentially transmissive envelope used in the device of the present invention is necessary to effectively obtain representative vapor samples from a vapor source phase. Use of the differentially vapor permeable envelope provides a device which is capable of sensing and indicating low levels of vapor or slight or slow changes in the vapor concentration whereas other devices, not having a differentially vapor permeable envelope, fail to accurately indicate the levels or changes of vapor concentration.

In a preferred embodiment of the present invention, there is provided a method and device for accurately and continuously monitoring and indicating parametric concentrations of selected volatile components in a soil phase. For example, the selected parametric concentration may be the minimum amount of soil moisture content necessary to keep a potted plant from wilting, or a deleterious concentration of ammonia in the soil or some other meaningful concentration. The device disclosed in the present invention overcomes the deficiencies of prior art wick-type devices since the device described herein can be used for monitoring soil moisture without requiring the presence of liquids within the device and particularly eliminates the use of wicks and the problems associated therewith.

The present inventor has discovered that the concentration of various volatile soil components in the upper levels of soil, for example the top 30 cm of soil, can be determined by analyzing the vapor released from the surface of the soil at the air-soil interface. The concentrations of these vapors can be empirically correlated with a corresponding concentration of the volatile components in the soil. These correlations can be used with the method and devices of the present invention to indicate selected parametric concentrations of volatile components in soil, and are particularly useful in indicating moisture available to shallow-rooted plants. The correlations for available moisture are useful for various types of soil ranging from heavy clay to light potting mix. Thus, although plants growing in a heavy clay may begin to wilt at lower absolute soil moisture concentrations than those growing in lighter, more loosely packed soil, the moisture in the soil which is effectively available to the plant can be correlated with the moisture available at the surface in the form of water vapor and is substantially independent of the soil type.

Similarly, a concentration of other volatile components in soil, such as ammonia, can be determined by measuring the level of the desired vapor component available at the surface of the soil and correlating this amount with the amount in the soil.

By choosing an appropriate standard, various desired parametric concentrations of volatile soil components can be indicated by the method and devices of this invention. Accordingly, one aspect of the present invention relates to a method for continuously monitoring the concentration of volatile soil components, particularly water, which comprises (1) sampling directly from the surface of the soil a representative portion of a selected vapor component released from the air-soil interface of the soil to be monitored, (2) comparing the vapor concentration in the sample with a standard which is representative of a parametric concentration of a corresponding volatile component in the soil, and (3) indicating the concentration of the vapor in the sample relative to the standard and thereby indicating the concentration of the corresponding volatile component in the soil. The method is particularly useful in monitoring available amounts of moisture and ammonia in soil containing shallow-rooted plants. In one embodiment the moisture vapor rising from the surface of the soil around a potted plant is sampled. The relative humidity of the moisture vapor is determined and compared to the relative humidity of moisture vapor rising from soil having a selected parametric concentration of moisture, such as the available moisture needed to sustain the life of a plant. The sampling and comparing process is continuous, and when the moisture vapor concentration in the sample is equal to or less than the standard concentration, the need for additional water in the soil is indicated, such as by a visible color change.

An aspect of the present invention also relates to particular devices adapted to rest on the surface of soil and continuously monitor and indicate the concentration of specific volatile components in the soil. The devices of the present invention include a sensing means and means for responsively coupling the sensing means directly to the surface of the soil so that a representative sample of the volatile components released at the air-soil interface are presented to the sensing means. The sensing means is capable of continuously comparing the concentration of a selected volatile component in the sample with a standard which is representative of a parametric concentration of a corresponding volatile component in the soil, and includes means for indicating the concentration of the selected volatile component in the soil. In one embodiment the device comprises in combination a sensing element overlying a flat base. A cover sheet having a viewing means, such as a transparent cover or a cover having a transparent window in register with the sensing element, overlies the sensing element. The edges of the cover sheet are joined to the base to form an envelope which closely conforms to the sensing element leaving a minimum of free space within the envelope.

The cover sheet and base must be permeable to vaporous components, but must be impermeable to liquids. The vapor transmission rate (expressed as vapor weight/unit area/unit time) of the base should be greater than the vapor transmission rate of the cover sheet.

The differentially vapor-permeable envelope formed by the cover sheet and the base, which can rest directly on the soil, serves to responsively couple the sensing element to the soil surface and is capable of sampling a representative portion of vapor released from the surface of the soil corresponding to a selected volatile soil component.

The sensing element comprises a vapor-responsive indicating component which is capable of continuously sensing a vapor sample and providing a detectable change in property, preferably a visible change in property such as a change in color, in response to changes in vapor concentration in the sample relative to a selected standard concentration. For example, where soil moisture is being monitored, the standard may be 75% R.H., which has been found to correlate with a parametric concentration representing the plant-life-sustaining available moisture in the soil. When the continuously monitored sample concentration changes from above to below the standard (or vise versa) indicating the change from above to below (or vice versa) a parametric concentration of moisture in the soil, a visible change in the color of the sensing element or some other detectable change in property may be effected. Thus, a material which changes color or visibly responds to a change in R.H. at the 75% level can be used as an effective indicating means.

Particularly useful as indicating components in the sensing elements are hydrated salts which change color in response to given changes in relative humidity or deliquescent compounds which exhibit a change in color or other optical properties in response to given changes in relative humidity. Alternatively, materials which are sensitive to other vapor components, such as ammonia, can be used for monitoring various soil volatiles.

While for most applications it is preferred to use a reversible sensing element, i.e. one that can repeatedly change a property, such as color, in response to repeated changes in vapor concentration, so that continuous monitoring can be achieved, for some applications the device can employ a sensing element which undergoes an irreversible change in response to exposure to a given vapor concentration. As noted previously, the differentially vapor-permeable envelope used in the monitoring device allows particularly effective continuous monitoring of subtle changes in vapor concentration and, accordingly, the use of a reversible sensing element provides a most advantageous combination in accordance with this invention.

The devices of the present invention are placed in intimate contact with the surface of the soil. The device can be used to monitor the concentration of volatile components in potted soil as well as unpotted soil and can be successfully used in determining the moisture and other volatile components available to potted plants as well as outdoor vegetation, such as grass or other shallow rooted plants. When the device is adapted to monitor the moisture content of soil, the device, in one embodiment, exhibits a given color when there is sufficient available water in the soil to sustain the life of the plant. When the available moisture in the soil approaches a selected parametric concentration, such as when the available moisture is insufficient to maintain the health of the plant, the indicating element changes color to warn that the soil surrounding the plant needs watering. When sufficient water has been added, the indicating element resumes its former color until the moisture concentration in the soil again approaches the parametric concentration. Different parametric concentrations can be indicated by employing various indicating elements which change color at characteristic vapor concentrations.

The invention can be further illustrated by reference to the specific embodiments shown in the drawings wherein.

Figure 1:
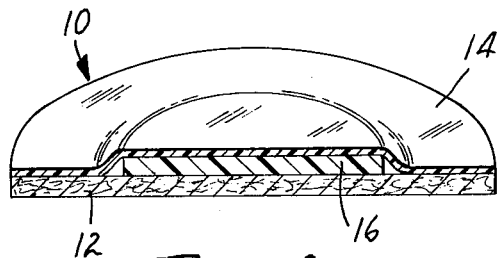
FIG. 1 is a perspective view partially in cross section of a monitoring device according to the present invention.

FIG. 1 shows one embodiment of a vapor monitoring device 10 comprising a sensing element 16 enclosed in a closely conforming envelope which comprises base 12 and cover 14. Base 12 is permeable to vapor, but is impermeable to soil and other solid or liquid components which may be present. Cover 14 is shown in FIG. 1 as being coextensive with base 12 and is joined to base 12 at the common periphery of base 12 and cover 14. The base 12 and cover 14 can be joined by conventional means such as by heat sealing or by the use of adhesives. Cover 14 is permeable to vapor, but is impermeable to bulk liquids or solids.

While base 12 and cover 14 are both permeable to vapor, cover 14 has a maximum vapor transmission rate which is less than the vapor transmission rate of base 12 so that the envelope formed by base 12 and cover 14 is differentially vapor permeable. The vapor transmission rate of the base would ideally be infinitely higher than the cover. The vapor transmission rate of the base should be at least 50% greater than that of the cover and preferably at least about 100% greater than that of the cover.

The minimum vapor transmission rate of the cover should be sufficient to allow a reasonably quick response time. Generally the response time for the monitoring device should be about 15 minutes or less. For example, for monitoring moisture vapor issuing from soil, the minimum rate of water vapor transmission (WVT) of cover 14 should be about 2 g/1000 cm$^2$/24 hours, and the maximum WVT can be as high as about 60 g/1000 cm$^2$/24 hours. Preferably cover 14 has a WVT in the range of about 20 to 40 g/1000 cm$^2$/24 hours. Base 12 must have a minimum WVT of at least about 3g/1000 cm$^2$/24 hours, and preferably at least about 40 g/1000 cm$^2$/24 hours. Corresponding rates can be readily determined for monitoring other vapors.

Cover 14 should be transparent or be provided with other means for observing sensing element 16 such as a window in register with sensing element 16.

Sensing element 16 includes an indicating component which provides a detectable change in property in response to given changes in the vapor concentration within the envelope, such as a visible change in color, and will be described in greater detail hereinafter As noted previously, base 12 must be permeable to vapor and impermeable to bulk liquids or solids. Materials which meet this requirement are vapor permeable or microporous polymeric films or alternatively hydrophobic porous pads, such as an oil-absorbent, polypropylene microfiber mat. These microfiber mats are known in the art as exemplified in U.S. Pat. No. 3,847,821 (Column 5). The vapor permeable films which can be used for base 12 or cover 14 are well known in the art. Polymeric materials such as cellulose polymers and copolymers, polyesters, polyethers, polyurethanes, polyalkylenes, polyacetates and the like which have the required vapor transmission properties can be used. Microporous polyester and polyether urethanes can also be used. Cellulose acetate is particularly preferred as a cover material for devices monitoring moisture vapor. As noted previously, these materials should not transmit bulk water, and therefore excessively hydrophilic polymers such as hydrophilic polyoxyethylene polyurethane polymers should not be used in the devices of this invention.

The aforementioned characteristics of base 12 are critical to the successful operation of device 10. If base 12 is permeable to liquid water or is constructed so as to wick water into contact with sensing element 16, the device will provide erroneous indications due to the presence of the liquid water in contact with the sensing element. In addition, the liquid water may tend to leach indicating component from sensing element 16, shortening the useful life of the monitoring device 10. Thus, base 12 is not a wick material as used in prior art devices, and in fact must be hydrophobic or otherwise impermeable to bulk liquid for the device of the present invention to operate successfully. The liquid impermeability of device 10 is particularly advantageous when the monitoring device is to be used for potted plants, wherein the device may be subjected to periodic flooding during watering of the plant.

As shown in FIG. 1, cover 14 should closely conform to the sensing element 16 so as to minimize the free space in the envelope defined by cover 14 and base 12. Minimizing the free space helps to prevent condensation of moisture within the envelope.

Sensing element 16 includes an indicating component which alone, or in combination with other portions of the sensing element, exhibits a detectable change in property in response to changes in concentration of specific vapor components relative to a selected standard. It is preferred that the indicating component of sensing element 16 be capable of exhibiting a visible change such as a change in color or optical properties. Alternatively, the indicating component can exhibit non-visible changes which can be detected such as a change in conductivity, permeability, density, crystalline form, and the like.

For devices used to monitor soil moisture, chemicals, such as hydrated salts, which visibly respond to changes in relative humidity by changing color, are particularly suitable. A preferred hydrated salt is cobalt chloride ($CoCl_2.6H_2O$). This salt, when applied to or absorbed in a cellulosic material, gelatin, silica gel, or polymeric material, can change from a pink to a blue color depending on the level of the relative humidity to which the salt is exposed. These salts are well known and have been used in various humidity indicating means as described in U.S. Pat. Nos. 2,460,071, 2,580,737, 3,702,755 and 3,788,128.

Salt mixtures comprising cobalt chloride with other materials can also be used as indicating components of sensing element 16. Mixtures of cobalt chloride with cobalt thiocyanate (e.g. equal parts by weight) have been used to provide a visible color change in the relative humidity range of about 50 to 75 percent R.H. U.S. Pat. Nos. 2,460,074 and 3,788,128 describe the use of these salt mixtures as humidity indicating materials. This combination of chemicals can be used to provide a pink color at relative humidities above about 75%. When the relative humidity goes below 75% the indicating material gradually changes to a lavendar color, becoming blue at a relative humidity of about 50% and below. The humidity at which the color change occurs can be adjusted by varying the ratio of cobalt chloride to cobalt thiocyanate. For example, a sensing element can be prepared by saturating a piece of porous filter paper, such as Whatman No. 1 filter paper, with a 20% aqueous composition of equal parts by weight cobalt chloride and cobalt thiocyanate and drying the saturated filter paper. The response range of the sensing element can be varied to some degree by controlling the concentration of salt in the sensing element.

A useful indicating component which exhibits a detectable color change over a relatively narrow relative humidity range comprises a mixture of cobalt chloride with a copolymer of polyvinyl pyrrolidone/vinyl acetate ("I 535," General Analine and Film). Copolymer to cobalt chloride ratios of about 6:1 to about 1:1 are preferred. The mixture is dissolved in water and absorbed in or applied to an absorbent pad or other carrier, and when dried provides a sensing element which exhibits a readily observable color change in the 70% to 80% relative humidity range.

In one embodiment of the device 10 shown in FIG. 1 the sensing element 16 is prepared by applying an indicating component directly to the underside of cover 14. For example, the cobalt chloride/copolymer solution described above can be coated on the underside of cover 14 in the form of a dot or other shape having a diameter of about 0.5 to 1.5 centimeters. After the solution dries, the coating which forms sensing element 16 is ready for use.

In yet another embodiment sensing element 16 can include as the indicating component a deliquescent compound which exhibits a reversible change in the optical properties at a given level of relative humidity. For example, the sensing element 16 can comprise a coherent, continuous layer of deliquescent compound which is opaque at humidity levels below the point at which the compound deliquesces and which becomes optically transparent on deliquescing, together with a layer underlying the deliquiescent compound which is at least partially colored in contrast to the opaque compound so as to be observable, and preferably conspicuous, when the compound deliquiesces and becomes transparent.

When the surrounding humidity is below a given level, the deliquescent compound remains opaque and the underlying layer is not visible. When the humidity rises above the point at which the compound deliquesces, the compound becomes transparent and the underlayer is visible, preferably conspicuous, to the observer, thereby indicating exposure to a selected level of relative humidity within the envelope. When the humidity level within the envelope is again lowered below the deliquescent point of the compound, the compound effloresces and again becomes opaque and the underlayer is no longer visible to the observer. In one embodiment the underlayer can be a contrasting color or can have intelligence printed on the surface thereof so that when the deliquescent compound becomes transparent a conspicuous color or an appropriate message such as "wet" or the like is observed.

A preferred means of providing a continuous layer of deliquescent compound is to absorb a solution of the deliquescent compound in a thin layer of tissue paper and dry the paper. Sodium bromide is a preferred deliquescent salt, although other deliquescent compounds known in the art are suitable. The sensing element 16 which includes sodium bromide as the deliquescent compound provides a change in optical properties when the relative humidity within the envelope is about 57%.

When the device 10 is used to monitor the concentration of vapor components other than moisture, e.g. ammonia, the sensing element 16 comprises indicating components capable of responding to changes in the concentration of these specific volatile components. For example, a device for monitoring the ammonia concentration of soil can be provided by employing alizarin or pH papers sensitive to the 3 - 5.5 pH range such as are available commercially under the trade name "pHydrion" papers from Micro Essential Laboratory. Indicators employing the "pHydrion" papers visibly respond by changing color from yellow/orange to blue/green, which color change is correlative to the ammonia concentration (in parts per million) in the soil.

In addition, by selecting a sensing element which responds to other specific vapors, the monitoring device may be used to detect and monitor the concentration and change in concentration of various vapors such as the oxides of nitrogen, sulfur and carbon, and the halogens.

Figure 2:
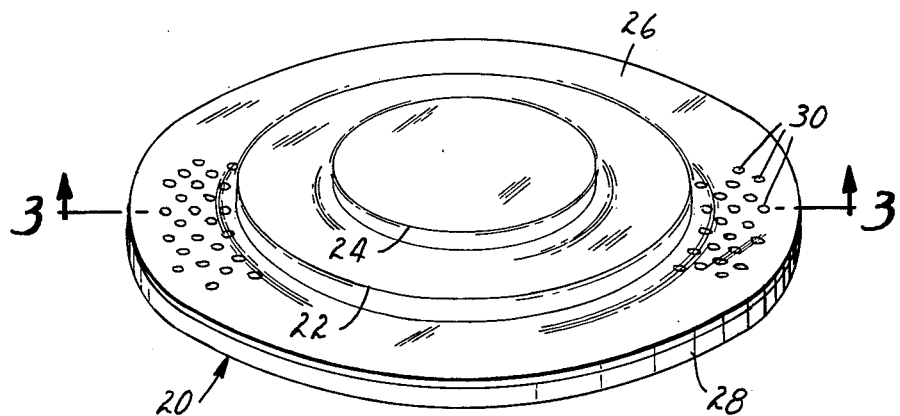
FIG. 2 is a perspective view of an alternate embodiment of the disclosed monitoring device.

FIG. 2 is an alternate embodiment of a vapor monitoring device according to the present invention. Monitoring device 20 is similar to that shown in FIG. 1 comprising vapor permeable base 22, sensing element 24, and vapor permeable cover 26. Device 20 also contains a protective layer 28 underlying base 22 and containing pores 30. Layer 28 and cover 26 are shown extending beyond base 22 and are joined at their periphery to enclose base 22 and sensing element 24 in a closely conforming envelope. Protective layer 28 is shown as a porous layer which is permeable to vapor and which may be permeable to liquid water since base 22 and cover 26 are impermeable to liquids and protect sensing element 24. Protective layer 28 serves to protect base 22 during handling and helps prevent base 22, particularly when base 22 is a porous mat of blown microfibers, from becoming clogged with dirt and the like. Representative of materials which can be used for protective layer 28 are porous polyethylene films such as 3M Brand "TRANSPORE" tape and a microporous tape having a non-woven backing such as 3M Brand "MICROPORE" tape, both available commercially from the 3M Company.

Figure 3:
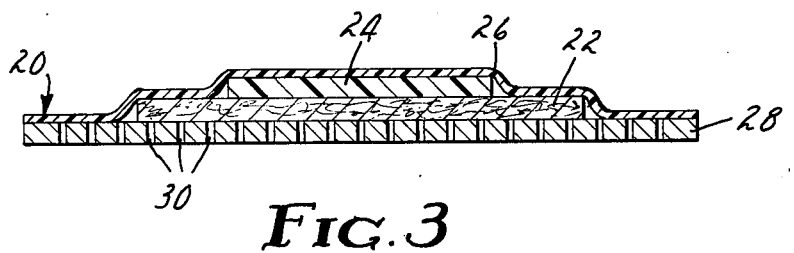
FIG. 3 is a cross section along line 3—3 of the monitoring device shown in FIG. 2.

FIG. 3 is a cross section along line 3—3 of the monitoring device shown in FIG 2. As can be seen, cover 26 together with base 22 and protective layer 28 envelop and closely conform to sensing element 24, minimizing the free space within the envelope surrounding sensing element 24.

In order to operate successfully as a monitoring device 10, 20, the sensing element 16, 24 shown in FIGS. 1-3 must be responsively coupled to the vapor source phase at the interface so that the monitoring device can accurately sample and compare a representative surface vapor concentration. This is achieved in the present invention by enclosing the sensing element 16, 24 in a sampling envelope defined by base 12 and cover 14 as in FIG. 1, or by base 22 and cover 26 as in FIG. 2. The sampling envelope shown in FIG. 3 is adapted to rest on, and intimately contact, the surface of the vapor source phase, such as the soil surrounding a potted plant, collect a representative sample of vapors released from the surface of the phase, and present the sample to sensing element 16, 24.

Due to the difference in vapor transmission rates between the cover 14, 26 and the base 12, 22 a sudden change in vapor input through base 12, 22 will not cause the interior of the envelope to become immediately overwhelmed with or starved of vapor; that is, the vapor concentration within the envelope may be slightly different than the actual vapor concentration of the base-vapor source phase interface until steady state is achieved. This lagging response tends to reduce any effect of transient peaks and valleys of vapor concentration released from the vapor source phase.

Further, the relatively slow vapor transmission rate of the cover 14 prevents the vapors entering the envelope through the base 12, 22 from being overwhelmed by vapors entering through the cover 14, 26 from the surrounding atmosphere. Temporary changes in relative humidity in the surrounding environment will have little or no effect on a sensing element sensitive to changes in relative humidity. However, constant operation at humidity levels above the selected standard relative humidity, e.g. above 75% R.H., which has been found to be a useful R.H. Standard, may ultimately overcome the monitoring device and impair the ability of the device to accurately indicate the selected parametric moisture concentration.

Although cover 14, 26 is relatively less permeable than base 12, 22, the cover must have the aforementioned minimum vapor transmission rate. If cover 14, 26 does not have the necessary vapor transmission rate, moisture or other vapors can accumulate within the envelope and allow undesirable condensation in the envelope, causing the sensing element 16, 24 to be contacted by bulk liquid which can leach chemicals from the sensing element or cause a false reading by a humidity sensitive element.

The monitoring device of the present invention should be large enough to sample vapor released from a representative area of the vapor source phase. Discs about 1.25 to 5 cm in diameter have been found sufficient to provide accurate results. Shapes other than discs can be used with equivalent results.

A disc of about 2.5 cm in diameter is an effective compromise size to achieve convenient handling and accurate sampling. This allows the device to accumulate vapors released from about 5 cm² of the surface of the vapor source phase.

Because the vapors reside in the monitoring device for a short period of time before passing through the cover, some mixing of the vapors takes place and the monitoring device, in effect, averages the concentration of vapor with time and over the area covered by the device and can provide a more accurate reading than a wick or other point sampling device can provide.

Generally monitoring devices having a base area of less than about 1.25 cm² are not preferred since the device becomes difficult to observe and handle and does not sample a large enough area of the vapor source phase surface. Monitoring devices which have a base area of greater than about 20 cm² can function effectively but may be too large for some applications, for example, they may be difficult to fit into small quarters such as a small flower pot or may be unsightly in a small flower pot.

Figure 4:
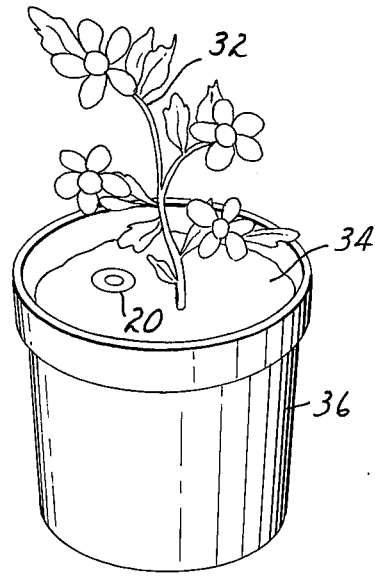
FIG. 4 is a perspective view of a potted plant showing a monitoring device such as that shown in FIG. 3 positioned on the soil in close proximity to the plant.

When used for monitoring the available moisture content of soil around potted plants, the monitoring device is located on the surface of the soil in close proximity to the potted plant as shown in FIG. 4. When the plant is watered and the soil has sufficient moisture, the sensing element which is visible through the cover has a detectable characteristic property such as a characteristic color. As the moisture is taken from the soil by the plant and by evaporation and reaches a parametric concentration, e.g. the moisture concentration determined to be just above that at which the plant will wilt, the relative humidity within the device will fall to a level below the selected standard, e.g. 75% R.H., and the sensing element changes a detectable property, e.g. color. This change indicates the need for additional water in the soil. The addition of water to the soil so that the moisture concentration in the soil rises above the parametric amount causes the initial detectable property, e.g. the initial color, of the sensing element to return after a short equilibration period.

Because the monitoring device protects the sensing element from bulk liquid, plants can be watered with the monitoring device in position next to the plant, although it is preferred to have the monitoring device removed during watering. In tests using the monitoring device of the present invention to regulate the watering schedule of a wide variety of plants in both heavy and light soils, the plants thrived and did not suffer from overwatering, as did plants which had their watering schedules fixed by prior art, wick-type devices.

The monitoring devices are useful to detect and indicate the presence of moisture in other environments. Particularly the monitoring devices have proven useful in detecting the presence of certain levels of liquids in body dressings such as diapers and surgical dressings, thereby eliminating the need to touch or remove the articles for examination. This is particularly useful where the body dressings have a liquid-impermeable outer covering, e.g. polyethylene film, and the presence of moisture is not detectable by touching the outer surface of the dressing. A monitoring device, similar to that shown in FIGS. 1–3 or having other shapes, can be attched to the dressing with the base resting on the dressing and the cover disposed outwardly of the dressing and the body to which it is applied. When the body dressing becomes moist, the monitoring device can indicate, e.g. change color, when the moist condition exists.

Where the body dressing has a vapor permeable covering, e.g. polyethylene, the monitoring device can be incorporated into the dressing using a portion of the outer covering of the dressing as the cover of the monitoring device.

The monitoring devices can also be used to detect and indicate vapors from decomposing matter in solid and liquid phases. For example, a monitoring device having a sensing element which is responsive to ammonia can be placed on proteinaceous matter such as fish, and the concentration of ammonia produced by decomposition detected and indicated. Alternatively, the indicators can be floated on a pool of liquid such as sewage or other effluent streams and detect and indicate vapors dissolved therein or produced by decomposition within the liquid.

The following examples will serve to illustrate the practice of the method and the use of the vapor monitoring devices of the present invention.

EXAMPLE 1

To demonstrate the utility of the monitoring device in indicating the need for watering a potted plant at proper intervals, a monitoring device was prepared as in FIGS. 2 and 3 wherein protective layer 28 was a 2.5 cm diameter disc of a microporous polyethylene film (3M brand "TRANSPORE" tape, 3M Company), pad 22 was an oil sorbent pad of blown polypropylene microfibers, sensing element 24 comprising a mixture of equal parts hydrated cobalt chloride and cobalt thiocyanate absorbed in a disc of No. 1 Whatman filter paper. Cover 26 was a piece of cellulose acetate film (3M brand "Magic Mending" tape, No. 810, 3M Company) adhesively bonded to protective layer 28.

Several zebra plants (Aphelandra) were potted in 15 cm diameter foamed plastic azalea pots 13 cm deep. A light potting soil of equal parts peat and vermiculite (Terra-Lite "Redi-Earth", W. R. Grace Co.) was used for some plants, while a heavier clay loam was used for others. Zebra plants were used because they are particularly sensitive to moisture and prone to wilting if given insufficient water.

The plants were kept indoors at room temperature (22° C) at a fairly constant relative humidity of about 20% R.H. with fluorescent lighting.

The plants were properly watered so the surface of the soil was moist and the monitoring devices were placed next to some of the plants on the leveled soil surface. The plants were watered during the remainder of the test.

The color of the monitoring devices changed from the original pink color to a visibly detectable lavender color after about 11 days for the plants in the light soil and after 7 days for the plants in the heavy soil (corresponding to a humidity level within the monitoring device of about 70–75% R.H.). The weight % moisture in the top 2.5 cm of soil and the bottom 10 cm of soil in each pot was then separately determined.

Other plants were monitored by employing the common method of touching the soil surface. When the surface was dry to the touch (6 days heavy soil, 10 days light soil) the weight % moisture in the top 2.5 cm and bottom 10 cm of soil was determined.

Plants containing wick-type indicators were also tested and the soil moisture measured as above when the need for water was indicated (1 day heavy soil, 7 days light soil).

In addition, some soil samples were allowed to dry to the point where the plants wilted (12 days heavy soil, 17 days light soil) and the moisture in the top 2.5 cm of soil then determined.

The results of the moisture tests were as follows:

| | Weight % Moisture in Soil | | | | | |
| --- | --- | --- | --- | --- | --- | --- |
| | Heavy Soil | | | Light Soil | | |
| Monitoring Device Used | Top 2.5 cm | Bottom 10 cm | Time | Top 2.5 cm | Bottom 10 cm | Time |
| 1. Wick-Type Device | 21% | 22% | 1 day | 74% | 75% | 7 days |

-continued

| Monitoring Device Used | Weight % Moisture in Soil | | | | | |
|---|---|---|---|---|---|---|
| | Heavy Soil | | | Light Soil | | |
| | Top 2.5 cm | Bottom 10 cm | Time | Top 2.5 cm | Bottom 10 cm | Time |
| 2. Touch | 12% | 16% | 6 days | 62% | 67% | 10 days |
| 3. Monitoring Device of the Present Invention | 9% | 14% | 7 days | 57% | 65% | 11 days |
| 4. Wilting | 6% | — | 12 days | 46% | — | 17 days |

The above data indicate that the monitoring device of the present invention can be used to accurately indicate a parametric concentration of moisture in soil, i.e. in this case the point at which the plant needs water before wilting, and can closely approximate the point at which an experienced horticulturalist would indicate need for water.

The wick-type devices indicated the plant required water before the moisture level was sufficiently low to require water.

EXAMPLE 2

A False Aralia (Dizygotheca elegantissima) plant about 1 meter high was potted in a pot 25 cm in diameter and 20 cm deep containing a sandy loam soil and exposed to the condition of light, temperature, and relative humidity as in Example 1. Touch tests indicate this plant should be watered about every 9 days under these conditions in order to thrive.

A monitoring device was prepared as in Example 1 and placed on level soil in the pot near the plant. The initial pink color changed to lavender in a period of between 9 and 10 days. Upon watering the soil to saturation the color changed back to pink after about 15 – 30 minutes and remained pink for another period of 9–10 days, and then again changed to lavender, and the watering repeated.

After 3 months of this repeated watering cycle, the plant was thriving.

EXAMPLE 3

Monitoring devices were prepared as in Example 1 except that the sensing elements comprised 3 – 5.5 pH "pHydrion" papers (Micro Essential Laboratory).

Soils having various ammonia content were placed in polyethylene bags, the monitoring devices placed on the leveled surface of the soil within the bags, and the bags sealed. After 90 minutes the indicators were observed on each soil sample. The ammonia content of the soils were confirmed by analysis. The results were as follows:

| Soil Sample No. | Indicator Color | Soil Ammonia Content, ppm |
|---|---|---|
| 1 | Dark green/blue | 7.8 |
| 2 | Green | 4.8 |
| 3 | Faint green/yellow | 1.8 |
| 4 | Yellow/orange | Not detected |

The monitoring devices were successful in differentiating between soil samples having differing ammonia content.

EXAMPLE 4

A disposable diaper having a polyethylene liquid impermeable covering was modified by cutting a hole in the outer covering and attaching a monitoring device similar to that described in Example 1 over the hole with the base of the device adjacent the diaper fabric. The diaper was then applied to a baby in the conventional manner. When the diaper became wet with urine, the sensing element changed from blue to pink indicating the need for changing the diaper.

EXAMPLE 5

A monitoring device like that described in Example 3 was used to indicate the state of decomposition of crabmeat. Three samples of crabmeat were obtained. The first sample was fresh; the second evidenced some decomposition but was still edible; while the third was decomposed to a point where the meat was not edible. Twenty to fifty gram samples were placed in glass beakers, the base of the monitoring devices placed on the crabmeat samples, and the beakers covered.

After one hour the monitoring device on the first sample showed no color change, while the device on the second sample had turned slightly green at the edges of the sensing element. After 10 minutes the sensing element of the device on the third sample had turned completely green. Thus, the monitoring device can be used to accurately detect and indicate unwanted or dangerous decomposition in food products by detecting the vapors issuing therefrom.

What is claimed is:

1. A device for monitoring and indicating the concentration of a vapor at a phase interface comprising
   a. a sensing means for comparing the concentration of a selected vapor component in a sample with a standard which is representative of a selected parametric concentration of said vapor in said sample, said sensing means including means for indicating the concentration of said vapor in said sample relative to said standard, and
   b. a differentially vapor permeable, liquid impermeable envelope enclosing said sensing means to responsively couple said sensing means to a vapor source phase at said phase interface, said envelope comprising a base adapted to rest on said vapor source phase and a cover for said base, said base and said cover vapor permeable defining a sealed, closely conforming envelope containing said sensing means, said cover having a vapor transmission rate equivalent to a water vapor transmission rate of between 20 and 60 grams/1000 cm$^2$/24 hours, said base having a vapor transmission rate at least 50% greater than the vapor transmission rate of said cover, said cover adapted for viewing said indicating means.

2. A device according to claim 1 wherein said sensing means comprises an indicating component capable of visibly responding to changes in the concentration of a selected vapor component.

3. A device according to claim 2 wherein said selected vapor component is ammonia.

4. A device according to claim 2 wherein said selected vapor component is water vapor.

5. A device according to claim 4 wherein said indicating component comprises cobalt chloride.

6. A device according to claim 5 wherein said sensing means is adapted to change color at a relative humidity between 50 and 75%.

7. A device according to claim 4 wherein said indicating component is a deliquescent salt capable of reversibly changing from an opaque to a transparent state in response to a change in relative humidity.

8. A soil monitoring device according to claim 4 wherein said base is a vapor permeable hydrophobic pad.

9. A soil monitoring device according to claim 8 wherein said device also includes a porous protective sheet underlying said base.

10. A soil monitoring device according to claim 9 wherein said indicating component comprises a mixture of cobalt chloride and polyvinyl pyrrolidone/vinyl acetate copolymer.

11. A soil monitoring device according to claim 9 wherein said sensing element is a film of indicating component comprising a mixture of cobalt chloride and polyvinyl pyrrolidone/vinyl acetate copolymer, said film adhered directly to said cover sheet.

12. A device according to claim 4 wherein said cover of said envelope has a water vapor transmission rate in the range of about 20 g/1000 cm$^2$/24 hours to about 40 g/1000 cm$^2$/24 hours.

13. A body dressing comprising an aqueous liquid absorbent layer and a liquid impervious layer, said body dressing including a monitoring device according to claim 1 located adjacent said absorbent layer, at least a portion of said liquid impervious layer being transparent so that said monitoring device can be viewed therethrough.

14. A method of continuously monitoring the concentration of vapor at a phase interface which comprises
 a. continuously collecting a representative vapor sample in a differentially vapor permeable, liquid impermeable, envelope directly from a vapor source phase at the phase interface, said envelope comprising a base and a cover vapor permeable, said cover having a vapor transmission rate equivalent to a water vapor transmission rate of between 20 and 60 grams/1000 cm$^2$/24 hours;
 b. comparing the concentration of a selected vapor component in said sample with a standard contained in said envelope which is representative of a selected parametric concentration of said vapor in said sample; and
 c. visibly indicating the concentration of said vapor in said sample relative to said standard.

15. A method according to claim 14 wherein said vapor component is water vapor.

16. A method according to claim 15 wherein said vapor source phase is soil containing a potted plant and said parametric vapor concentration is indicative of the minimum life-sustaining soil moisture concentration necessary for said potted plant.

17. A method according to claim 13 wherein said envelope comprises a cover having a water vapor transmission rate of from about 20 g/1000 cm$^2$/24 hours to about 40 g/1000 cm$^2$/24 hours and a base having a water vapor transmission rate at least 50% greater than said cover.

* * * * *

UNITED STATES PATENT AND TRADEMARK OFFICE
CERTIFICATE OF CORRECTION

PATENT NO. : 4,063,452
DATED : December 20, 1977
INVENTOR(S) : Thomas Ian Bradshaw It is certified that error appears in the above-identified patent and that said Letters Patent are hereby corrected as shown below:

Column 14, line 53, insert the words -- vapor permeable -- before the word "cover", per the Amendment After Final Rejection, and line 54, the words --vapor permeable -- (erroneously inserted in this line instead) should be deleted.

Column 16, line 10, "vapor permeable" should be inserted before "cover" instead of after,
line 28, change "claim 13" to -- claim 16 --.

Signed and Sealed this

Twenty-ninth Day of August 1978

[SEAL]

Attest:

RUTH C. MASON
Attesting Officer

DONALD W. BANNER
Commissioner of Patents and Trademarks